United States Patent [19]

Fix et al.

[11] Patent Number: 4,749,694

[45] Date of Patent: Jun. 7, 1988

[54] NOVEL LYSINE ESTERS USED AS ABSORPTION

[75] Inventors: Joseph A. Fix; Stefano A. Pogany, both of Lawrence, Kans.

[73] Assignee: Merck & Co., Inc., Rahway, N.J.

[21] Appl. No.: 604,349

[22] Filed: Apr. 26, 1984

[51] Int. Cl.⁴ ........................................... A61K 31/545
[52] U.S. Cl. ........................................ 514/40; 514/28; 514/32; 514/36; 514/38; 514/39; 514/41; 514/200; 514/201; 514/202; 514/203; 514/204; 514/206; 514/208; 514/551
[58] Field of Search .................. 560/169; 424/246; 514/40, 28, 32, 36, 38, 39, 41, 200, 201, 202, 203, 204, 206, 208

[56] References Cited

U.S. PATENT DOCUMENTS

| | | | |
|---|---|---|---|
| 3,433,779 | 3/1959 | Vogler | 560/169 |
| 4,154,956 | 5/1979 | Ueda | 560/169 |
| 4,296,095 | 10/1981 | Hoppe | 560/169 |

FOREIGN PATENT DOCUMENTS

| | | |
|---|---|---|
| 5767513 | 10/1980 | Japan . |
| 1476432 | 6/1977 | United Kingdom . |
| 1477672 | 6/1977 | United Kingdom . |

OTHER PUBLICATIONS

Roche, "Design of Biopharmaceutical Properties Through Prodrugs and Analogs," pp. 281–315 (1977).

*Primary Examiner*—Michael L. Shippen
*Attorney, Agent, or Firm*—Manfred Polk; Michael C. Sudol

[57] ABSTRACT

Novel lysine esters used as absorption enhancing agents for gastrointestinally and rectally administered drugs. Also provided are processes for preparation of said lysine ester compounds as well as pharmaceutical formulations and methods for their use as absorption enhancing agents.

7 Claims, No Drawings

NOVEL LYSINE ESTERS USED AS ABSORPTION

BACKGROUND OF THE INVENTION

This invention relates to novel lysine esters used as absorption enhancing agents and to methods for their preparation. More particularly, it relates to absorption enhancing agents comprising lysine ester compounds and to methods for the preparation and use of the absorption enhancing agents for increasing rectal and gastrointestinal tract absorption of drugs.

DESCRIPTION OF THE PRIOR ART

The prior art describes numerous drugs which are only slowly absorbed rectally and from the gastrointestinal tract. Consequently, said drugs must be administered by an intravenous or intramuscular route or in excessively large oral doses in order to attain clinical efficacy. As an example, the β-lactam antibiotics constitute one class of antibiotics which is poorly absorbed by the oral route. Similarly, the glycosidic and related antibiotics, which are chemically characterized by a chemical structure which includes a carbohydrate moiety bonded to the remainder of the molecule by a glycosidic linkage, are poorly absorbed by the oral route. The glycosidic and related antibiotics, such as macrolide, aminoglycoside, lincomycin, anthracycline and other chemically related antibiotics, are poorly absorbed from the gastrointestinal tract because of two properties: hydrophilicity and/or acid instability. The hydrophilic, polar nature of these antibiotics precludes their rapid absorption so that even the small percentage which is absorbed is subject to a long residency time in the acidic gastric environment.

Oral and rectal drug administration have advantages over other routes of drug administration, such as parenteral or topical administration. Many drug substances that are given parenterally have restricted use in that they are usually administered by trained personnel in hospitals or clinics. Oral or rectal drug administration does not require highly trained personnel and represents significantly less hazardous conditions to patients, such as possible antigenicity development with certain drugs (e.g., hormones). It is therefore clear that any factor or agent which enhances the rate of rectal or gastrointestinal tract absorption will demonstrate improved clinical efficacy.

SUMMARY OF THE INVENTION

In accordance with this invention, there are provided novel absorption enhancing agents of the following general formula:

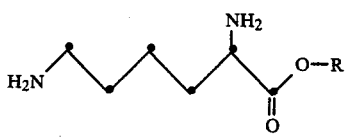

wherein R is an alkyl radical consisting of 5 to 22 linear or branched chain carbon atoms.

Accordingly, it is an object of the invention to provide new compounds that are useful for increasing absorption of drugs when administered rectally or gastrointestinally to patients (human and animal).

A further object of the invention is to provide methods for the preparation of these novel compounds.

Another object of the invention is to provide pharmaceutical compositions for administering these lysine ester compounds which provide the following:

(a) to enhance the bioavailability of drugs administered rectally or gastrointestinally by administering therewith a lysine ester absorption enhancing agent, and (b) to provide a stable dosage form utilizing a novel class of lysine ester absorption enhancing agents which when administered rectally or gastrointestinally will provide an increased blood level of the therapeutic agent.

A still further object of the invention is to provide a lysine ester promoter of rectal and gastrointestinal tract drug absorptions in concentrations which do not alter the normal morphology of the mucosal cells.

These and other objects and advantages of the present invention will become apparent from the following description.

DETAILED DESCRIPTION OF THE INVENTION

The invention is concerned with novel absorption enhancing agents which have been found to have significant absorption promoting activity and are very useful for enhancing rectal and gastrointestinal absorption of drugs. The novel absorption enhancing agents may be best described as comprising a compound of the following general structural formula:

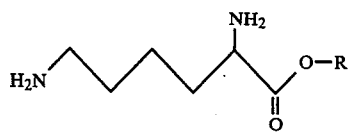

wherein R is an alkyl radical consisting of 5 to 22 linear or branched chain carbon atoms. The compounds of formula (I) are prepared by condensing the amino acid N-α-ε-di-t-Boc-L-lysine of the formula:

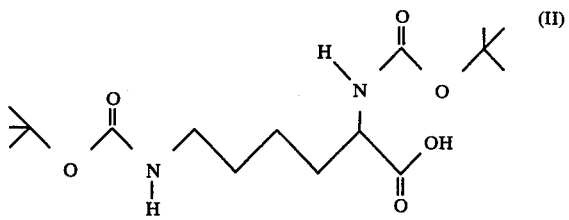

with an alcohol of the general formula (R—OH) wherein R is an alkyl radical (linear or branched) having from 5 to 22 carbon atoms. The preparation of the compound (I) of the present invention takes place according to conventional esterification methods. It is preferable to operate in the presence of inert solvents, for example dichloromethane, and dehydrating agents for removal of water, such as N,N'-dicyclohexylcarbodiimide at room temperature. The removal of the t-butyloxycarbonyl protective groups from the amino terminals on the lysine moiety is accomplished by stirring in dioxane containing 10% of 2.5N hydrochloric acid at room temperature.

The compounds, according to the present invention of general formula (I), have a basic character and therefore, can form pharmacologically compatible salts with acids. For the preparation of acid-addition salts, the compounds of formula (I) are reacted, preferably in an organic solvent, with one or two equivalents of a pharmacologically compatible inorganic or organic acid, for example, hydrochloric acid, hydrobromic acid, phosphoric acid, acetic acid, and the like.

We have discovered that the esters of general formula (I) and the pharmacologically compatible salts thereof have the property of being able to promote rectal and gastrointestinal tract absorption of certain drug substances that are not by themselves capable of being absorbed. In addition, it has been shown that the absorption promoting effect of the esters of general formula (I) and the pharmacologically accepted salts thereof, as exemplified by hexadecyl lysinate, act in a concentration dependent manner (Example 9). Based on this information, the compounds of the instant invention are effective at doses of greater than or equal to 0.75 mg/dose. The compounds (I) have the added desirable characteristic of possessing no known pharmacological activity and of being non-damaging to the intestinal mucosa, as evidenced by the reversibility of the absorption promoting effect (Example 10). Another important advantage of compounds (I) is the fact that, on a weight or dose burden basis, they are more active than other known absorption promoters (e.g., EDTA and salicylate). At a 5 mg/dose level, EDTA and salicylate are ineffective, while hexadecyl lysinate increases the intestinal absorption of sodium cefoxitin from 1% to 12%.

Specific compounds of the present invention include the following:
pentyl lysinate
hexyl lysinate
heptyl lysinate
octyl lysinate
nonyl lysinate
decyl lysinate
undecyl lysinate
dodecyl lysinate
tridecyl lysinate
tetradecyl lysinate
pentadecyl lysinate
hexadecyl lysinate
heptadecyl lysinate
octadecyl lysinate
nonadecyl lysinate
eicosyl lysinate
heneicosyl lysinate
docosyl lysinate Various active agents provide beneficial effects when administered to patients. Such agents which can be made more useful by enhancing its absorption in accordance with this invention, are exemplified by, but not limited to, the following classes of agents:

(1) β-Lactam antibiotics such as cefoxitin, N-formamidinylthienamycin, amoxicillin, ampicillin, azlocillin, bacampicillin, carbenicillin, cefaclor, cefadroxil, cefamandole, cefaparole, cefatrizine, cefazoline, cefonicid, cefaperazone, ceforanide, cefotaxime, cefotiam, cefroxadine, cefsulodin, ceftazidime, ceftizoxime, cephalaxin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G, penicillin V, pivampicillin, piperacillin, pirbenicillin and the like.

(2) Aminoglycoside antibiotics such as gentamycin, amikacin, astromicin, betamicin, butikacin, butirosin, clindamycin, josamycin, kanamycin, neomycin, netilmicin, tobramycin and the like.

(3) Antiviral and antineoplastic agents such as ara C (cytarabine), acyclovir, floxuridine, rabavirin, vidarabine, idoxuridine, trifluridine and the like.

(4) Amino acids such as methyldopa, carbidopa, levodopa, fludalamine and the like.

(5) Muscle relaxants such as theophylline, cyclobenzaprine, aminophylline, diphylline, oxtriphylline, ambuphylline, fenethylline, guathylline, pentoxyfylline, xanthinol niacinate, theophylline glycinate, glucophylline and the like.

(6) Polypeptides such as cyclo-(N-Ala-Tyr-D-Trp-Lys-Val-Phe)acetate (No. 363,586), somatostatin, insulin, gastrin, caerulein, cholecystokinin and the like.

(7) Anti-inflammatory agents such as indomethacin, sulindac, ibuprofen and the like.

(8) Diuretics such as aldactone, hydrochlorothiazide, amiloride, amiloride and hydrochloride and the like.

The enhancement of drug absorption in accordance with this invention is not by any means limited to the above drugs, but are in general applicable to other classes of drugs such as analgesics, anabolics, androgens, anorexics, adrenergics, antiadrenergics, antiallergics, antibacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radio-nuclide diagnostic agents and the like.

The amount of drug varies over a wide range, but in general the therapeutically effective unit dosage amount of the selected drug depends on that amount known in the art to obtain the desired results.

Generally, the amount of adjuvant employed in the practice of this invention ranges from 0.75-100 mg in each unit dose. The percentage of adjuvant in the total combination of drug plus adjuvant is 5-99% with a preferred ratio of adjuvant in the total combination of adjuvant plus drug being 10-40%.

For gastrointestinal tract administration, the formulations may be prepared as liquids, suspensions, capsules, tablets, coated tablets, and other standard procedures known in the art. The preferred formulation is a compressed tablet composed of a minimum of 0.75 mg lysine ester with the pharmacologically required dose of drug and sufficient excipients to formulate an acceptable composition. For rectal application, the formulations may be prepared as microenemas, suppositories, rectal tablets, and other standard procedures known in the art. The preferred formulation is a solid suppository composed of a minimum of 0.75 mg lysine ester with the pharmacologically required dose of drug and sufficient suppository base to formulate an acceptable composition. The methods and choice of excipients and suppository bases are well known to those skilled in the art and the composition of said formulations is not limited to compressed tablets or solid suppositories by this invention.

As to the pharmaceutically acceptable salts, those coming within the purview of this invention include the pharmaceutically acceptable acid-addition salts. Acids useful for preparing these acid-addition salts include, inter alia, inorganic acids, such as hydrochloric, hydrobromic, sulfuric, and phosphoric acids, and organic acids such as maleic, fumaric, tartaric, citric, 2-acetoxybenzoic, salicyclic, succinic, or methanesulfonic acids.

The following examples illustrate preparation of various novel compounds and compositions of the invention. The examples should be construed as illustrations rather than limitations thereof.

EXAMPLE 1

Hexyl lysinate

2 G (5.8 mmol) of N,N'-di-t-Boc-L-lysine free carboxylic acid and 0.59 g (5.8 mmol) of hexanol are combined in 30 mL of dichloromethane. To the stirred solution at 25° C. is added 1.2 g (5.8 mmol) of dicyclohexylcarbodiimide followed by 80 mg (0.65 mmol) of 4-dimethylaminopyridine as an acylation catalyst. The reaction is complete in about 10 minutes as shown by TLC analysis (silica gel plate, solvent 20% EtOAc/$CH_2Cl_2$) which revealed total consumption of starting materials and formation of a new, major spot. Solid materials are removed by filtration and the solvent is evaporated to give crude material which after chromatography on silica gel (eluting with 20% EtOAc/$CH_2Cl_2$) yielded 2.35 g (91% yield) of a colorless oil homogeneous by TLC. This oil was placed in 25 mL of dioxane and 2.5N hydrochloric acid (3 mL) was added. The mixture was stirred at 25° C. for 1 day; the solvents were evaporated to dryness under vacuum. Ethyl ether and ethanol were added and sequentially removed under vacuum several times to remove residual hydrochloric acid. Finally, the product was recrystallized from a mixture of ethanol and ether. The ester obtained in this procedure is isolated as the dihydrochloride salt.

EXAMPLE 2

Decyl lysinate

Following the procedure outlined in Example 1 but substituting decanol for hexanol, decyl lysinate dihydrochloride was obtained.

EXAMPLE 3

Tetradecyl lysinate

Following the procedure outlined in Example 1 but substituting tetradecanol for hexanol and removing the t-butyloxycarbonyl (t-Boc) protective groups with hydrogen chloride gas in ether, tetradecyl lysinate dihydrochloride was obtained.

EXAMPLE 4

Hexadecyl lysinate

As in Example 1 but with hexadecanol to obtain hexadecyl lysinate dihydrochloride.

EXAMPLE 5

Docosyl lysinate

As in Example 1 but with docosanol to obtain docosyl lysinate dihydrochloride.

EXAMPLE 6

The absorption of sodium cefoxitin, a β-lactam antibiotic, was tested in rats employing aqueous formulation of sodium cefoxitin with or without various alcohol-lysine esters as absorption promoting agents. The solutions were formulated at pH 7 and administered in a total volume of 250 μl to the duodenal area of the rat small intestine or rectal compartment. Blood samples were collected, sodium cefoxitin assayed, and "area-under-the-curve"* calculated. Percent bioavailability was determined versus intravenous administration. Each animal received 2.5 mg sodium cefoxitin ±5.0 mg alcohol-lysine ester. From 3 to 12 animals were used for each compound.

*"area-under-the-curve" is the integrated area of the time versus serum concentration profile. It is a standard technique used to quantitate drug absorption in terms of bioavailability.

| Alcohol-lysine Ester | Percent Cefoxitin Bioavailability (mean ± SE) | |
|---|---|---|
| | Duodenal | Rectal |
| None | 1 | 2 ± 1.1 |
| Hexyl lysinate | — | 3 ± 0.9 |
| Decyl lysinate | 27 ± 15.7 | 71 ± 3.2 |
| Tetradecyl lysinate | 12 ± 4.2 | 49 ± 2.1 |
| Hexadecyl lysinate | 12 ± 3.1 | 51 ± 4.5 |
| Docosyl lysinate | 11 ± 2.0 | 22 ± 3.0 |

EXAMPLE 7

The absorption of cyclo-(N-Ala-Tyr-D-Trp-Lys-Val-Phe)acetate (No. 363,586), a polypeptide compound, was tested in rats employing aqueous formulations of No. 363,586 with or without various alcohol-lysine esters as absorption promoting agents. The solutions were formulated at pH 6 and administered in a total volume of 250 μl to the duodenal area of the rat small intestine or rectal compartment. Blood samples were collected, No. 363,586 assayed, and "area-under-the-curve"* calculated. Percent bioavailability was determined versus intravenous administration. Each animal received 0.1 mg No. 363,586 ±5.0 mg alcohol-lysine ester. From 3–6 animals were used for each compound.

*"area-under-the-curve" is the integrated area of the time versus serum concentration profile. It is a standard technique used to quantitate drug absorption in terms of bioavailability.

| Alcohol-lysine Ester | Percent No. 363,586 Bioavailability (mean ± SE) | |
|---|---|---|
| | Duodenal | Rectal |
| None | 1 | 7 ± 3.5 |
| Hexyl lysinate | — | 17 ± 2.8 |
| Decyl lysinate | 8 ± 3.5 | 36 ± 5.1 |
| Tetradecyl lysinate | 7 ± 3.0 | 33 ± 23.0 |
| Hexadecyl lysinate | 24 ± 8.6 | 100 ± 46.5 |
| Docosyl lysinate | 10 ± 0.9 | 10 ± 1.3 |

EXAMPLE 8

The absorption of cytarabine, an antineoplastic and antiviral agent, was tested in rats employing aqueous formulations of cytarabine and hexadecyl lysinate. The compounds were administered in a total volume of 250 μl at pH 6. Both rectal and duodenal sites in the intestine were tested. Blood samples were collected, cytarabine assayed, and "area-under-the-curve"* calculated. Percent bioavailability was determined versus intravenous administration. Each animal received 2.5 mg cytarabine ±5.0 mg hexadecyl lysinate. Three animals were used for each experiment.

*"area-under-the-curve" is the integrated area of the time versus serum concentration profile. It is a standard technique used to quantitate drug absorption in terms of bioavailability.

| Adjuvant | Percent Cytarabine Bioavailability (mean ± SE) | |
|---|---|---|
| | Duodenal | Rectal |
| None | 5 | 6 ± 1.7 |
| Hexadecyl lysinate | 24 ± 6.4 | 60 ± 4.3 |

EXAMPLE 9

The absorption of sodium cefoxitin, a β-lactam antibiotic, was tested in rats employing aqueous formulations of sodium cefoxitin with varying concentrations of hexadecyl lysinate as an absorption promoting agent. The solutions were formulated at pH 6 and administered in a total volume of 250 μl to the duodenal area of the rat small intestine or the rectal compartment. Blood samples were collected, sodium cefoxitin assayed, and "area-under-the-curve"* calculated. Percent bioavailability was determined versus intravenous administration. Each animal received 2.5 mg sodium cefoxitin with varying amounts of hexadecyl lysinate. From 3–6 animals were used for each study.

*"area-under-the-curve" is the integrated area of the time versus serum concentration profile. It is a standard technique used to quantitate drug absorption in terms of bioavailability.

| Hexadecyl lysinate (mg/body) | Percent Cefoxitin Bioavailability (mean ± SE) | |
|---|---|---|
| | Duodenal | Rectal |
| 0 | 1 | 2 ± 1.1 |
| 0.125 | — | 14 ± 6.0 |
| 0.750 | 3 ± 1.2 | 35 ± 4.2 |
| 1.25 | 9 ± 2.9 | 44 ± 3.7 |
| 2.5 | 13 ± 2.6 | 47 ± 8.7 |
| 5.0 | 12 ± 3.1 | 51 ± 4.5 |

EXAMPLE 10

The absorption of sodium cefoxitin, a β-lactam antibiotic, was tested in rats employing aqueous formulations of sodium cefoxitin. The sodium cefoxitin was administered either simultaneously with or 60–120 minutes after administration of a hexadecyl lysinate solution. Each rat received 2.5 mg sodium cefoxitin and 5.0 mg hexadecyl lysinate in a total volume of 250 μl, applied to the duodenal region or the rectal compartment. Formulations were adjusted to pH 6. Blood samples were collected, sodium cefoxitin assayed, and the "area-under-the-curve"* calculated. Percent bioavailability was determined versus intravenous administration. Three animals were used for each study.

*"area-under-the-curve" is the integrated area of the time versus serum concentration profile. It is a standard technique used to quantitate drug absorption in terms of bioavailability.

| Time of Administration (min) | | Percent Cefoxitin Bioavailability (mean ± SE) | |
|---|---|---|---|
| Hexadecyl Lysinate | Sodium Cefoxitin | Duodenal | Rectal |
| 0 | 0 | 12 ± 3.1 | 57 ± 4.5 |
| 0 | 60 | 6 ± 0.8 | 9 ± 4.3 |
| 0 | 120 | 1 ± 0.4 | 8 ± 2.3 |

What is claimed is:

1. A pharmaceutical composition for enhancing rectal and gastrointestinal absorption of an orally or rectally administered formulation comprising: (A) a therapeutically effective dosage amount of an antibiotic selected from the group consisting of cefoxitin. N-formamaidinylthienamycin, amoxicillin, ampicillin, azlocillin, bacampicillin, carbenicillins, cefaclor, cefadroxil, cefamandole, cefaparole, cefatrizine, cefazoline, cefonicid, cefaperaxzone, ceforanide, cefotazine, cefotiam, cefroxadine, cefsulodin, ceftazidime, ceftizoxime, cephalaxin, cephaloglycin, cephaloridine, cephradine, cyclacillin, cloxacillin, dicloxacilin, floxacillin, hetacillin, methicillin, nafcillin, oxacillin, sarmoxacillin, sarpicillin, talampicillin, penicillin G, penicillin V, pivampicillin, piperacillin, and pirbenicillin, gentamycin, amikacin, astromicin, betamicin, butikacin, butirosin, clindamycin, josamycin, kanamycin, neomycin, nitilmicin and tobramycin; and (B) a lysine ester absorption enhancing agent of the formula:

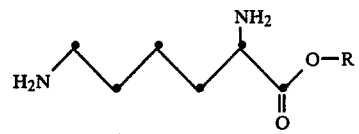

wherein R is an alkyl radical consisting of 5 to 22 linear or branched chain carbon atoms.

2. The composition of claim 1 wherein the drug is cefoxitin.

3. The composition of claim 1 wherein the drug is gentamycin.

4. The composition of claim 1 further comprising pharmaceutically acceptable excipients.

5. A method of enhancing the rate of rectal and gastrointestinal absorption of an orally or rectally administered composition comprising administering a therapeutically effective dosage amount of: (A) an antibiotic selected from the group consisting of cefoxitin, N-formamidinylthiennamycin, amoxicillin, ampicillin, azlocillin, bacampicillin, carbenicillin, cefalor, cefadroxil, cefamandole, cefaparole, cefatrizine, cefazoline, cefonicid, cefaperazone, ceforanide, cefotaxime, cefotiam, cefroxadine, cefsulodin, ceftaziine, ceftizoxime, cephalaxin, cephaloglycin, cephaloridine, cephradine, cyclacillin, cloxacillin, dicloxacillin, floxacillin, hetacillin, methicillin, nafcillin, oxacillin, sarmoxacillin, sarpicillin, talampicillin, ticaricillin, penicillin G, penicillin V, pivampicillin, piperacillin, pirbenicillin, gentamycin, amikacin, astromicin, betacicin, butikacin, butirosin, clindamycin, josamycin, kanamycin, neomycin, netilimicin and tobramycin; and (B) a lysine ester absorption enhancing agent of the formula:

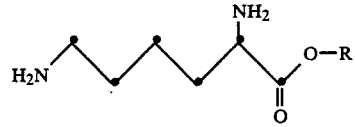

wherein R is an alkyl radical consisting of 5 to 22 linear or branched chain carbon atoms.

6. The method of claim 5, wherein the drug is cefoxitin.

7. The method of claim 5, wherein the drug is gentamycin.

* * * * *